(12) United States Patent
Cousin

(10) Patent No.: US 11,302,441 B2
(45) Date of Patent: Apr. 12, 2022

(54) PATIENT TREATMENT RESOURCE UTILIZATION PREDICTOR

(71) Applicant: 3M INNOVATIVE PROPERTIES COMPANY, St. Paul, MN (US)

(72) Inventor: Larry D. Cousin, South Jordan, UT (US)

(73) Assignee: 3M Innovative Properties Company, St. Paul, MN (US)

(*) Notice: Subject to any disclaimer, the term of this patent is extended or adjusted under 35 U.S.C. 154(b) by 0 days.

(21) Appl. No.: 17/309,129

(22) PCT Filed: Oct. 22, 2019

(86) PCT No.: PCT/IB2019/059031
§ 371 (c)(1),
(2) Date: Apr. 28, 2021

(87) PCT Pub. No.: WO2020/089732
PCT Pub. Date: May 7, 2020

(65) Prior Publication Data
US 2022/0013218 A1 Jan. 13, 2022

Related U.S. Application Data

(60) Provisional application No. 62/751,838, filed on Oct. 29, 2018.

(51) Int. Cl.
*G16H 40/20* (2018.01)
*G16H 10/60* (2018.01)
*G16H 50/20* (2018.01)

(52) U.S. Cl.
CPC ............ *G16H 40/20* (2018.01); *G16H 10/60* (2018.01); *G16H 50/20* (2018.01)

(58) Field of Classification Search
CPC ......... G16H 40/20; G16H 10/60; G16H 50/20
See application file for complete search history.

(56) References Cited

U.S. PATENT DOCUMENTS 5,018,067 A 5/1991 Mohlenbrock
2008/0171916 A1 7/2008 Feder
(Continued)

FOREIGN PATENT DOCUMENTS

CN 107123072 9/2017
JP 2014182472 9/2014
(Continued)

OTHER PUBLICATIONS

Cousin, "Results of the Analysis of the See5 Tool, Relative to the PMX Project", 2018, pp. 1-103.
(Continued)

*Primary Examiner* — Michael Tomaszewski
*Assistant Examiner* — Jay M. Patel
(74) *Attorney, Agent, or Firm* — Brian Bender

(57) ABSTRACT

A computer implemented method includes obtaining a schema defining variables representing patient treatment experiences for one or more health conditions, obtaining data from historical patient treatment experiences, the data being arranged in accordance with the schema, training a machine learning system based on a training set of the data for a specified time-period, and generating a model from the trained machine learning system, the model being based on variables selected by the trained machine learning system to predict patient treatment experiences for the one or more health conditions.

19 Claims, 5 Drawing Sheets

(56) References Cited

U.S. PATENT DOCUMENTS

| | | | |
|---|---|---|---|
| 2011/0082712 | A1 | 4/2011 | Eberhardt, III |
| 2012/0215560 | A1* | 8/2012 | Ofek .................. G16H 10/00 705/3 |
| 2013/0191158 | A1 | 7/2013 | Fillmore |
| 2013/0232103 | A1 | 9/2013 | Saeed |
| 2016/0117468 | A1 | 4/2016 | Mankad |
| 2016/0300034 | A1 | 10/2016 | Huddar |
| 2016/0354039 | A1* | 12/2016 | Soto .................... A61B 5/74 |
| 2016/0378942 | A1 | 12/2016 | Srinivas |
| 2017/0004279 | A1 | 1/2017 | Pingali |
| 2017/0177808 | A1 | 6/2017 | Irwin |
| 2018/0226153 | A1 | 8/2018 | Rubenstein |
| 2019/0311220 | A1* | 10/2019 | Hazard ............. G06K 9/6257 |
| 2020/0143924 | A1* | 5/2020 | Ilan .................... G16H 20/30 |
| 2020/0273581 | A1* | 8/2020 | Wolf ............... G06K 9/00711 |

FOREIGN PATENT DOCUMENTS

| | | |
|---|---|---|
| WO | WO 2000-067189 | 11/2000 |
| WO | WO 2018-006004 | 1/2018 |

OTHER PUBLICATIONS

International Search Report for PCT International Application No. PCT/IB2019/059031, dated Jan. 17, 2020, 5 pages.

\* cited by examiner

PATIENT TREATMENT RESOURCE UTILIZATION PREDICTOR

CROSS REFERENCE TO RELATED APPLICATIONS

This application is a national stage filing under 35 U.S.C. 371 of PCT/IB2019/059031, filed Oct. 22, 2019, which claims the benefit of U.S. Provisional Application No. 62/751,838, filed Oct. 29, 2018, the disclosure of which is incorporated by reference in its/their entirety herein.

BACKGROUND

Managing a health care facility (or group of facilities—enterprise) such as a hospital can be a very complex task. Patients with various ailments that are admitted to the hospital may utilize different amounts of resources, such as length of stays, for treatment. Patients with the same ailments may also utilize different amounts of resources. Complications may increase the utilization of resources. Changes in the way patients are treated may be made in attempts to improve resource utilization. The results of such changes can be difficult to observe. It can also be difficult to compare the performance of various hospitals since no two hospitals are the same and may have very different processes, staff, equipment, patient demographics, and a multitude of other factors that may be different.

SUMMARY

A computer implemented method includes obtaining a schema defining variables representing patient treatment experiences for one or more health conditions, obtaining data from historical patient treatment experiences, the data being arranged in accordance with the schema, training a machine learning system based on a training set of the data for a specified time-period, and generating a model from the trained machine learning system, the model being based on variables selected by the trained machine learning system to predict patient treatment experiences for the one or more health conditions.

DETAILED DESCRIPTION

Figure 1:
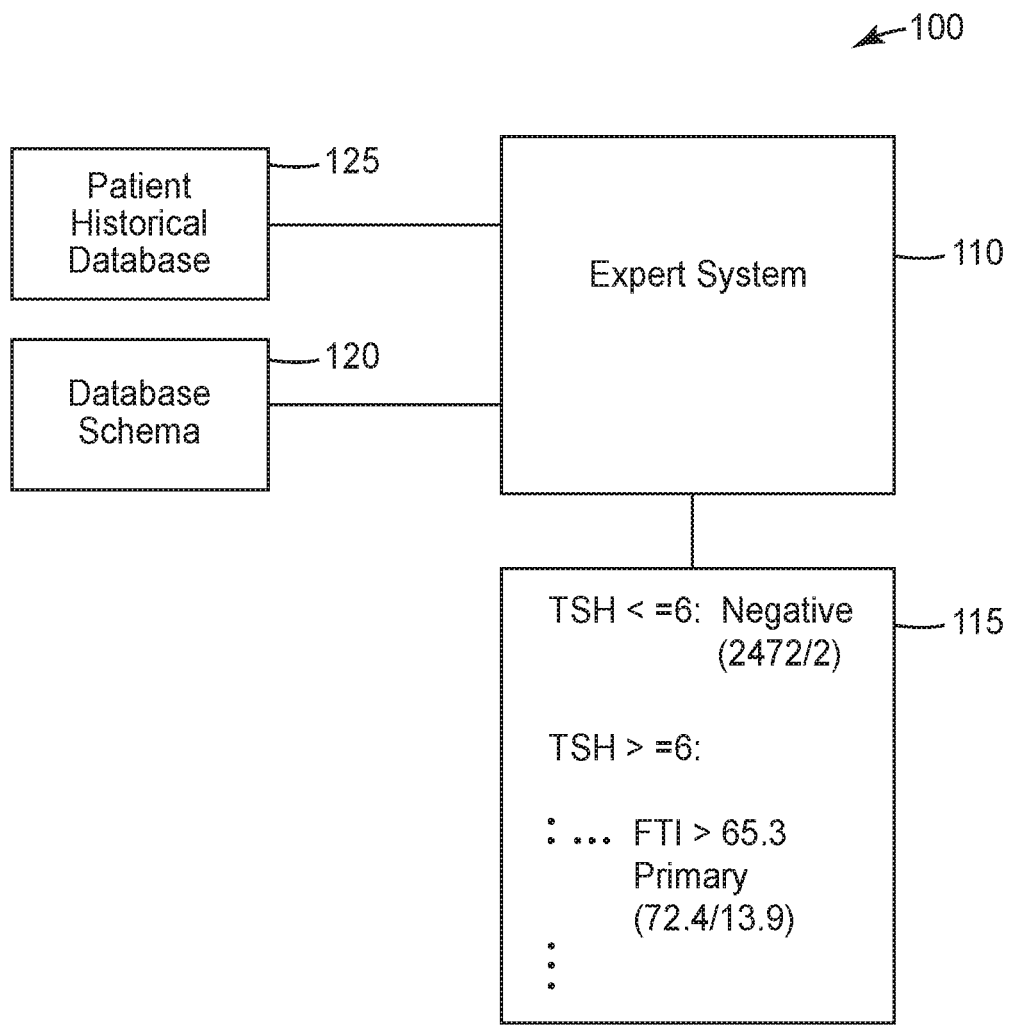
FIG. 1 is a block diagram of a database platform that utilizes a trained expert system to generate efficient decision trees to measure resource utilization according to an example embodiment.

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense, and the scope of the present invention is defined by the appended claims.

The functions or algorithms described herein may be implemented in software in one embodiment. The software may consist of computer executable instructions stored on computer readable media or computer readable storage device such as one or more non-transitory memories or other type of hardware-based storage devices, either local or networked. Further, such functions correspond to modules, which may be software, hardware, firmware or any combination thereof. Multiple functions may be performed in one or more modules as desired, and the embodiments described are merely examples. The software may be executed on a digital signal processor, ASIC, microprocessor, or other type of processor operating on a computer system, such as a personal computer, server or other computer system, turning such computer system into a specifically programmed machine.

The functionality can be configured to perform an operation using, for instance, software, hardware, firmware, or the like. For example, the phrase "configured to" can refer to a logic circuit structure of a hardware element that is to implement the associated functionality. The phrase "configured to" can also refer to a logic circuit structure of a hardware element that is to implement the coding design of associated functionality of firmware or software. The term "module" refers to a structural element that can be implemented using any suitable hardware (e.g., a processor, among others), software (e.g., an application, among others), firmware, or any combination of hardware, software, and firmware. The term, "logic" encompasses any functionality for performing a task. For instance, each operation illustrated in the flowcharts corresponds to logic for performing that operation. An operation can be performed using, software, hardware, firmware, or the like. The terms, "component," "system," and the like may refer to computer-related entities, hardware, and software in execution, firmware, or combination thereof. A component may be a process running on a processor, an object, an executable, a program, a function, a subroutine, a computer, or a combination of software and hardware. The term, "processor," may refer to a hardware component, such as a processing unit of a computer system.

Furthermore, the claimed subject matter may be implemented as a method, apparatus, or article of manufacture using standard programming and engineering techniques to produce software, firmware, hardware, or any combination thereof to control a computing device to implement the disclosed subject matter. The term, "article of manufacture," as used herein is intended to encompass a computer program accessible from any computer-readable storage device or media. Computer-readable storage media can include, but are not limited to, magnetic storage devices, e.g., hard disk, floppy disk, magnetic strips, optical disk, compact disk (CD), digital versatile disk (DVD), smart cards, flash memory devices, among others. In contrast, computer-readable media, i.e., not storage media, may additionally include communication media such as transmission media for wireless signals and the like.

FIG. 1 is a block diagram of a database platform 100 that utilizes a trained expert system 110 to generate decision trees 115 corresponding to a set of rules for a health care facility, such as a hospital, that can classify if a patient is out of norm in terms of resource utilization. The platform 100 may also be used to predict if a patient will go out of norm and require more or few resources to ensure proper treatment. The database utilizes a defined schema for training and testing data to provide accurate predictions while optimizing platform computing resources to measure health care facility resource utilization.

In one embodiment, the predictions correspond to a length of stay metric. In further embodiments many other metrics may be predicted, such as readmittance following a hospital stay, outpatient visits turning into a hospitalization, emergency room visits frequency, complication rate, expenditure, population emergency room visit rate, population hospital admission rate, etc. Each of these metrics correlate to consumption of health care facility resources, as well as patient care and experience. For instance, hospital readmission rates may be an indicator of quality of care. A readmission may result from incomplete treatment or poor care of the underlying problem or may reflect poor coordination of services at the time of discharge or afterwards. Readmissions are not only important indicators of quality, but also require additional resources to handle. Complications can also consume additional resources, including increasing length of stay for patients. Some complications are the result of a secondary diagnoses that may have been present on admission which affects the risk for complications. Some primary diagnoses are indicative of the risk for corresponding complications.

By classifying or predicting patient resource utilization, patients may be segmented by high vs. low utilization with the rules. Such segmentation facilitates identification of contributing common factors for patients to then predict how other people/populations will consume resources and costs. Knowledge of the contributing factors enables the provision of input to a health care provider, such as physician or nurse about a patient before they treat the patient so such providers are ready to deal with issues corresponding to the common factors identified before such issues manifest. The predictions may also identify likely issues that may arise during treatment to help a healthcare provider to be prepared for such issues.

The platform may utilize at least two input files. A database schema file 120 defines the data schema for the lines of input data and a data file 125 that contains the actual data records. The schema file may define the data structure for multiple patient conditions, including at least one condition a current patient may be experiencing. The following listing is an example See5 based schema for a hypothetical test system to diagnose one of the many potential conditions, a hypothyroid condition:

diagnosis.
age: continuous.
sex: M, F.
on thyroxine: f, t.
query on thyroxine: f, t.
on antithyroid medication: f, t.
sick: f, t.
pregnant: f, t.
thyroid surgery: f, t.
I131 treatment: f, t.
query hypothyroid: f, t.
query hyperthyroid: f, t.
lithium: f, t.
tumor: f, t.
goitre: f t.
hypopituitary: f, t.
psych: f, t.
TSH: continuous.
T3: continuous.
TT4: continuous.
T4U: continuous.
FTI:=TT4/T4U.
referral source: WEST, STMW, SVHC, SVI, SVHD, other.
diagnosis: primary, compensated, secondary, negative.
ID: label.

In the example schema, field variable names are in the left column, with types of values for variables specified in the right column. The field "age" has a continuous value indicative of the age of the patient. The field "sex" has a Male or Female designation. Other designations may be added in further examples. Many other fields have true/false value types show as "f,t". Other fields have values resulting directly from the field name, such as the field "referral source", which can have values corresponding to different doctors or health care facilities.

The example schema says that "diagnosis" is the dependent variable (which can take on the discrete values of primary, compensated, secondary, or negative) and all the other variables are the independent variables. Here is an example of the input training data records based on patient discharge data that correspond to the above schema for See5:

41,F,f,f,f,f,f,f,f,f,f,f,f,f,f,f,1.3,2.5,125,1.14,SVHC,negative,3733
23,F,f,f,f,f,f,f,f,f,f,f,f,f,f,f,4.1,2,102,?,other,negative,1442
46,M,f,f,f,f,N/A,f,f,f,f,f,f,f,f,f,0.98,?,109,0.91,other,negative,2965
70,F,t,f,f,f,f,f,f,f,f,f,f,f,f,f,0.16,1.9,175,?,other,negative,806
70,F,f,f,f,f,f,f,f,f,f,f,f,f,f,f,0.72,1.2,61,0.87,SVI,negative,2807
64,F,f,f,f,f,f,f,f,f,f,f,f,f,f,f,?,?,?,?,other,negative,1821
44,M,f,f,f,f,N/A,f,f,f,f,f,f,f,f,f,45,1.4,39,1.16,SVI,primary,2427
48,M,f,t,f,f,N/A,f,f,f,t,f,f,f,f,f,5.4,1.9,87,1,other,negative,1433
77,M,f,f,f,f,N/A,f,f,f,f,f,f,f,f,f,2,2.9,151,1.35,other,negative,942
27,F,f,f,f,f,f,f,f,f,f,f,f,f,f,f,2.6,?,112,1.15,other,negative,3266
65,M,f,f,f,f,N/A,f,f,f,f,f,f,f,f,f,14.8,1.5,61,0.85,SVI,compensated,251
27,F,f,f,f,f,f,f,f,f,f,f,f,f,f,f,15,1.6,82,0.82,SVI,compensated,2691
54,F,f,f,f,f,f,f,f,f,f,f,f,f,f,f,19,2.2,83,1.03,SVHC,compensated,822
68,M,f,f,f,f,N/A,f,f,f,f,f,f,f,f,f,2.4,1.6,83,0.89,SVI,negative,2534

The schema and the input are all in text format. The trained expert system produces a model, such as a decision tree in one embodiment. Other models may include deep neural network model, support vector models, and others. Some example expert systems may include See5, the DecisionTreeClassifier in a python package called scikit-learn, or the "tree" package in the R language to accomplish the same task. In further embodiments, other algorithms may be utilized to make predictions, such as random forest and boosting algorithms. It is easy to construct a decision tree that includes a set of rules that will exactly match an explicit set of data, but if new untrained data is later given, it will very likely not match the rules well in the future.

See5 tries to formulate rules that will model well (but probably not perfectly) the input data, and that will also model well later for new data. This is what is meant by not overfitting the data. The data is matched closely with the essence of the data, so that it will match future data as well—but not perfectly. Note that in the rules, variables from the source or input data are referred to as attributes.

Here are the results of running the full hypothyroid dataset through the trained expert system 110:

```
Class specified by attribute 'diagnosis'
Read 2772 cases (24 attributes) from hypothyroid.data
Decision tree:
TSH <= 6: negative (2472/2)
TSH > 6:
:...FTI <= 65.3: primary (72.4/13.9)
    FTI > 65.3:
    :...on thyroxine = t: negative (37.7)
        on thyroxine = f:
        :...thyroid surgery = t: negative (6.8)
            thyroid surgery = f:
            :...TT4 > 153: negative (6/0.1)
                TT4 <= 153:
                :...TT4 <= 37: primary (2.5/0.2)
                    TT4 > 37: compensated (174.6/24.8)
Evaluation on training data (2772 cases):
        Decision Tree
        ----------------
      Size      Errors
         7     10( 0.4%)   <<
      (a)   (b)   (c)   (d)    <-classified as
      ----  ----  ----  ----
       60    -3               (a): class primary
             154              (b): class compensated
                    -2        (c): class secondary
       -4    -1        2548   (d): class negative
Attribute usage:
    90% TSH
    18% on thyroxine
    16% thyroid surgery
    14% TT4
    13% T4U
    13% FTI
Evaluation on test data (1000 cases):
        Decision Tree
        ----------------
      Size      Errors
         7      3( 0.3%)   <<
      (a)   (b)   (c)   (d)    <-classified as
      ----  ----  ----  ----
       32                      (a): class primary
       -1    39                (b): class compensated
                               (c): class secondary
       -1    -1        926     (d): class negative
Time: 0.0 secs
```

The decision tree is shown above. For the training data, the generated decision tree produced a 0.4% error rate with 10 cases being misclassified out of the 2772 training cases. An evaluation test set of 1000 cases was also run against the generated decision tree which produced a 0.3% error rate (3 misclassified out of the 1000 cases). The evaluation data was not used to train the decision tree, simply to test it after creation. The decision tree may be implemented in linear code to run data through it in an automated manner.

In one embodiment, training may be boosted. In one example, the model created by training the expert system 100 is "boosted" with a 10-instance collaboration. Boosting works by the system generating different instances of the decision tree following slightly different generation philosophies. The final decision tree is then the combination voting of each different tree, where each have been individually run. The approach sometimes produces significant results. As in this case, the error rate on the training data is only 0.1%.

Some explanation would be useful for the format of errors that are produced for either the training data or test data for the expert system 110. The following shows the errors which are produced by the decision tree for the above hypothyroid example:

```
        Decision Tree
        ----------------
      Size      Errors
         7     10( 0.4%)   <<
      (a)   (b)   (c)   (d)    <-classified as
      ----  ----  ----  ----
       60    -3               (a): class primary
             154              (b): class compensated
                    -2        (c): class secondary
       -4    -1        2548   (d): class negative
```

The decision tree size is the number of branches in the tree that produce a dependent variable answer (in this case 7). The number of errors are the number of training/test cases that when run through the rules produce an incorrect answer. For the above case there are 10, which is the sum of the four red numbers in the small table below it. That table, "classified as", shows the 4 values of the dependent variable and, on each row, how many training/test cases produce the correct output (positive numbers or in black) and how many produce the incorrect (negative numbers or in red) output.

Consider the values for "primary". Sixty lines of training input when run through the rules produced the correct result of "primary". There were, however, 3 lines of input that produced "compensated" (because it is on the "primary" line, but the "compensated" column) as the output, but it should have been "primary". These 3 errors are thus type II (false-negative) errors relative to "primary". The decision tree also shows that the rules produced incorrect answers of "primary" for 4 training lines when those should have been "negative". Thus, those 4 cases where type I (false-positive) errors for "primary" but type II (false-negative) errors relative to "negative".

In one example set of tests, length of stay (LOS) stories were used to evaluate the system utilizing a machine learning system, such as See5. The dependent variable (the output answer) to model rules for is this: did an individual patient discharge contribute to the generation of a significant LOS story that shows that a hospital is out of the financial norm for some pattern of patient clinical situations. The independent variables are all the other patient attributes for a patient discharge. The variables starting with "PPC" followed by a number are codes corresponding to different conditions.

The following schema defines the patient attributes:
inStory.
recordID: label.
inStory: in, out.
facility: ignore.
APRDRG: discrete 317.
medSurg: med, surg.
serviceLine: discrete 41.
soiLevel: low, high.
SOI: U,L,M,H,X.
eligible: f,t.
actLOS: continuous.
expLOS: continuous.
cost: continuous.
admittedICU: f,t.
ICUdays: continuous.
AnyPPC: f,t.

PPCGroup1: f,t.|Extreme Complications
PPCGroup2: f,t.|Cardiovascular-Respiratory Complications
PPCGroup3: f,t.|Gastrointestinal Complications
PPCGroup4: f,t.|Perioperative Complications
PPCGroup5: f,t.|Infectious Complications
PPCGroup6: f,t.|Malfunctions, Reactions, etc.
PPCGroup7: f,t.|Obstetrical Complications
PPCGroup8: f,t.|Other Medical and Surgical Complications
PPC01: f,t.|Stroke & Intracranial Hemorrhage
PPC02: f,t.|Extreme CNS Complications
PPC03: f,t.|Acute Pulmonary Edema and Respiratory Failure without Ventilation
PPC04: f,t.|Acute Pulmonary Edema and Respiratory Failure with Ventilation
PPC05: f,t.|Pneumonia & Other Lung Infections
PPC06: f,t.|Aspiration Pneumonia
PPC07: f,t.|Pulmonary Embolism
PPC08: f,t.|Other Pulmonary Complications
PPC09: f,t.|Shock
PPC10: f,t.|Congestive Heart Failure
PPC11: f,t.|Acute Myocardial Infarction
PPC13: f,t.|Other Acute Cardiac Complications
PPC14: f,t.|Ventricular Fibrillation/Cardiac Arrest
PPC15: f,t.|Peripheral Vascular Complications Except Venous Thrombosis
PPC16: f,t.|Venous Thrombosis
PPC17: f,t.|Major Gastrointestinal Complications without Transfusion or Significant Bleeding
PPC18: f,t.|Major Gastrointestinal Complications with Transfusion or Significant Bleeding
PPC19: f,t.|Major Liver Complications
PPC20: f,t.|Other Gastrointestinal Complications without Transfusion or Significant Bleeding
PPC21: f,t.|*Clostridium difficile* Colitis
PPC23: f,t.|Genitourinary Complications Except Urinary Tract Infection
PPC24: f,t.|Renal Failure without Dialysis
PPC25: f,t.|Renal Failure with Dialysis
PPC26: f,t.|Diabetic Ketoacidosis & Coma
PPC27: f,t.|Post-Hemorrhagic & Other Acute Anemia with Transfusion
PPC28: f,t.|In-Hospital Trauma and Fractures
PPC29: f,t.|Poisonings Except from Anesthesia
PPC30: f,t.|Poisonings due to Anesthesia
PPC31: f,t.|Pressure Ulcer
PPC32: f,t.|Transfusion Incompatibility Reaction
PPC33: f,t.|Cellulitis
PPC34: f,t.|Moderate Infectious
PPC35: f,t.|Septicemia & Severe Infections
PPC36: f,t.|Acute Mental Health Changes
PPC37: f,t.|Post-Procedural Infection & Deep Wound Disruption Without Procedure
PPC38: f,t.|Post-Procedural Wound Infection & Deep Wound Disruption with Procedure
PPC39: f,t.|Reopening Surgical Site
PPC40: f,t.|Peri-Operative Hemorrhage & Hematoma without Hemorrhage Control Procedure or I&D Procedure
PPC41: f,t.|Peri-Operative Hemorrhage & Hematoma with Hemorrhage Control Procedure or I&D Procedure
PPC42: f,t.|Accidental Puncture/Laceration During Invasive Procedure
PPC44: f,t.|Other Surgical Complication—Moderate
PPC45: f,t.|Post-Procedural Foreign Bodies
PPC46: f,t.|Post-Procedural Substance Reaction & Non-O.R. Procedure for Foreign Body
PPC47: f,t.|Encephalopathy
PPC48: f,t.|Other Complications of Medical Care
PPC49: f,t.|Iatrogenic Pneumothorax
PPC50: f,t.|Mechanical Complication of Device, Implant & Graft
PPC51: f,t.|Gastrointestinal Ostomy Complications
PPC52: f,t.|Infection, Inflammation & Other Complications of Devices, Implants or Grafts Except Vascular Infection
PPC53: f,t.|Infection, Inflammation and Clotting Complications of Peripheral Vascular Catheters and Infusions
PPC54: f,t.|Central Venous Catheter-Related Blood Stream Infection
PPC59: f,t.|Medical & Anesthesia Obstetric Complications
PPC60: f,t.|Major Puerperal Infection and Other Major Obstetric Complications
PPC61: f,t.|Other Complications of Obstetrical Surgical & Perineal Wounds
PPC63: f,t.|Post-Procedural Respiratory Failure with Tracheostomy
PPC65: f,t.|Urinary Tract Infection
PPC66: f,t.|Catheter-Related Urinary Tract Infection
ageGroup: under65, 65to74, 75to84, over84.
weekendAdmit: f,t.
mondayDisch: f,t.
PACfacility: Home,HH,LTAC,Rehab,SNF.

"inStory" is the dependent variable that can have the values "in" or "out", meaning that this discharge (each line of data represents a single discharge) either contributed to a significant story ("in") or it didn't ("out"). An example of an in story is a length of stay that exceeded an average length of stay for a particular type of treatment that is normal for a particular healthcare facility. In other words, there is likely a story regarding why the patient had a longer stay than average. The average in various embodiments may be calculated for either a group of healthcare facilities run by an organization, or even an exemplary healthcare facility, such as a facility that has the best length of stay average of the group.

All the other variables are independent (even if they are truly not, they are considered to be) variables with various types and values. Some are of type "continuous" which means that they can have any numeric value. Some have discrete values like "f" or "t" (false or true) or some number of discrete values that are not explicitly designated. An example of this is "APRDRG: discrete 317." In this case, 317 unique DRGs are the inputs with values not explicitly defined.

Here is an example of the data that is being used to train the expert system that conforms to the schema defined above:

3,in,1,691,med,267,high,X,t,33,15.3,33630.21,t,32,f,f,f,f,
 f,f,f,f,f,f,f,f,f,f,f,f,f,f,f,f,f, f,f,f,f,f,f,f,f,f,f,f,f,
 f,f,f,f,f,f,f,f,f,f,f,f,f,f,f,f,f,f,f,f,75to84,f,f,Home
4,out,1,463,med,250,low,M,t,2,3.3,-2074.21,t,2,f,f,f,f,f,f,
 f,f,f,f,f,f,f,f,f,f,f,f,f,f,f,f,f,f,f,f,f,f,f,f,f,f,f,f,f,
 f,f,f,f,f,f,f,f,f,f, f,f,f,f,f,f,f,f,f,f,75to84,f,f,Home
5,out,1,5,surg,132,high,X,f,48,31.2,47623.08,f,0,t,f,f,t,f,
 f,f,f,f,f,f,f,f,f,f,f,f,f,f,f,f,f,t,f,f,f, f,f,f,f,f,f,f,f,f,f,f,
 f,f,f,f,f,f,f,f,f,f,f,f,f,f,f,f,f,f,65to74,f,t,Home
6,in,1,139,med,296,high,H,t,16,5.3,18313.35,t,2,t,f,f,f,f,t,
 f,f,f,f,f,f,f,f,f,f,f,f,f,f,f,f,f,f,f,f, f,f,f,f,f,f,f,f,f,t,f,
 f,f,f,f,f,f,f,f,f,f,f,f,f,f,f,f,f,f,t,f,75to84,t,f,HH 7,out,1,440,surg,387,high,H,t,7,8.1,-7780.65,t,4,f,f,f,f,f,f,
f,f,f,f,f,f,f,f,f,f,f,f,f,f,f,f,f,f,f,f,f,f,f,f,f,f,f,f,f,f,f,
f,f,f,f,f,f,f,f,f,f, f,f,f,f,f,f,f,f,f,f,f,under65,f,f,Home
8,out,1,315,surg,274,low,M,t,2,2.5,-3017.95,f,0,f,f,f,f,f,f,
f,f,f,f,f,f,f,f,f,f,f,f,f,f,f,f,f,f,f,f,f,f,f,f,f,f,f,f,f,f,f,
f,f,f,f,f,f,f,f,f,f, f,f,f,f,f,f,f,f,f,f,f,f,75to84,f,f,HH
9,out,1,260,surg,132,high,H,t,8,10.5,-6780.92,t,3,f,f,f,f,f,
f,f,f,f,f,f,f,f,f,f,f,f,f,f,f,f,f,f,f,f,f,f,f,f,f,f,f,f,f,f,f,
f,f,f,f,f,f,f,f,f,f, f,f,f,f,f,f,f,f,f,f,f,f,75to84,f,f,HH
10,in,1,321,surg,274,low,L,t,8,1.6,42241.93,f,0,f,f,f,f,f,f,
f,f,f,f,f,f,f,f,f,f,f,f,f,f,f,f,f,f,f,f, f,f,f,f,f,f,f,f,f,f,f,f,f,f,
f,f,f,f,f,f,f,f,f,f,f,f,f,f,f,f,f,f,f,under65,f,f,Home
11,out,1,120,surg,133,high,H,t,8,11.0,-8036.00,t,8,f,t,f,
f,f,f,f,f,f,f,t,f,f,f,f,f,f,f,f,f,f,f,f,f,f,f,f,f,f,f,f,f,f,f,
f,f,f,f,f,f,f,f,f,f,f,f,f,f,f,f,f,f,f,f,f,75to84,f,f,HH
12,out,1,301,surg,274,high,H,t,3,5.0,-9297.61,t,3,t,f,f,f,f,
f,f,f,t,f,f,f,f,f,f,f,f,f,f,f,f,f,f,f,f,f,f,t,f,f,f,f,f,f,f,f,f,
f,f,f,f,f,f,f,f,f,f,f,f,f,f,f,f,f,f,f,f,f,75to84,f,f,SNF
13,out,1,55,med,255,low,M,t,6,3.3,5987.63,t,6,f,f,f,f,f,f,
f,f,f,f,f,f,f,f,f,f,f,f,f,f,f,f,f,f, f,f,f,f,f,f,f,f,f,f,f,f,f,f,f,
f,f,f,f,f,f,f,f,f,f,f,f,f,f,f,f,f,75to84,f,f,SNF For this data the "recordID" is just a sequential number and does not correspond to any real identifier. "facility" is always the number 1, so there is no PHI in these records.

Figure 2:
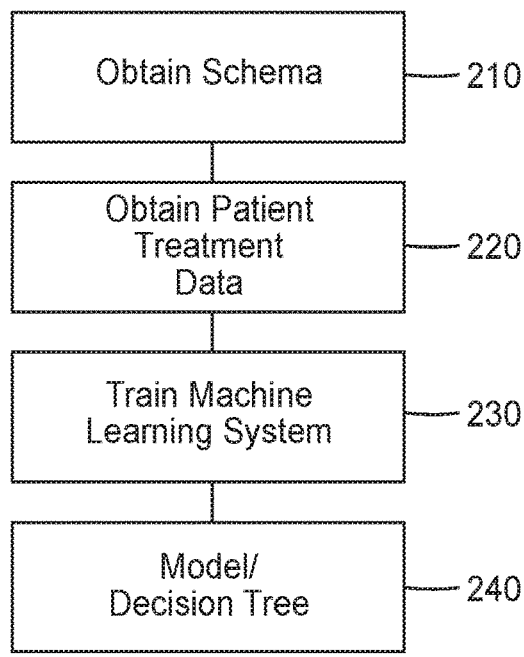
FIG. 2 is a flowchart illustrating a computer implemented method of predicting resource utilization in the treatment of patients according to an example embodiment.

FIG. 2 is a flowchart illustrating a computer implemented method 200 of predicting resource utilization in the treatment of patients according to an example embodiment. At operation 210, a schema is obtained defining variables, also referred to as attributes in the resulting model, representing patient treatment experiences for one or more health conditions. Data is obtained at operation 220. The data includes data from historical patient treatment experiences and is arranged in accordance with the schema. A machine learning system is trained at operation 230 based on a training set of the data for a specified time-period. At operation 240, a model, such as a decision tree is generated from the trained machine learning system. The decision tree is generated based on attributes selected by the trained machine learning system to predict patient treatment experiences for the one or more health conditions.

The decision tree may be pruned as a function of attribute usage in the decision tree. The decision tree may also be boosted by generating multiple different decision trees from the trained machine learning system and combining results from the multiple different decision trees to predict patient treatment experiences for the one or more health conditions.

In some embodiments, the data may be stored in a database in accordance with a schema defining the data including a dependent variable name and corresponding discrete value selected from a set of discrete values, a first set of multiple independent variables having corresponding discrete values, and at least one independent variable having a corresponding continuous value.

The treatment experiences in one example includes a length of stay corresponding to a patient treatment procedure. The data may correspond to a single healthcare facility, and the specified time-period may include a time-period starting from a time following a change in procedures at the single healthcare facility.

Figure 3:
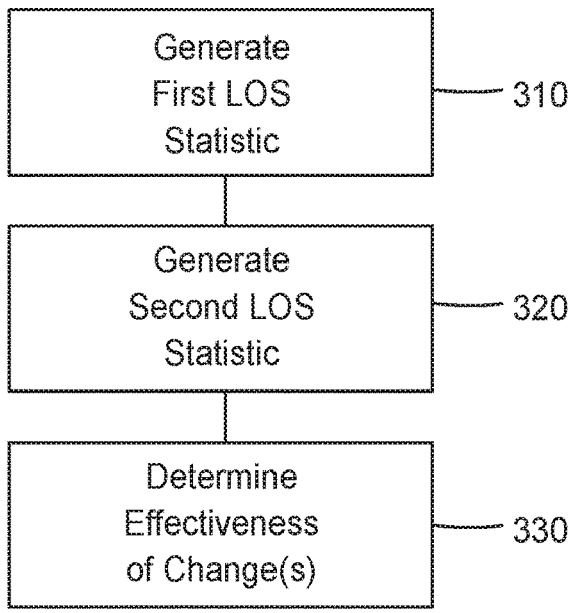
FIG. 3 is a flowchart illustrating a method of evaluating the effectiveness of changes made to procedures in the healthcare facility according to an example embodiment.

FIG. 3 is a flowchart illustrating a method 300 of evaluating the effectiveness of changes made to procedures in the healthcare facility. The changes may be generated based on analysis of the training data by other systems, or by human analysis in various embodiments. In method 300, the decision tree may be used at operation 310 to generate a first length of stay statistic for a first time-period prior to the change in procedures and also to generate at operation 320 a second length of stay statistic for a second time-period following the change in procedures. Note that in some embodiments, expert system 110 is trained separately for each of the different time-periods, and a corresponding model, such as a decision tree, is generated for each different time-period. Operation 330 is used to determine the effectiveness of the change in procedures as a function of the length of stay statistics. If the length of stay is about the same, the changes likely did not help improve resource utilization. If the length of stay increased, the changes were likely counterproductive. If the length of stay decreased over the second time-period, the changes were likely very effective. In any event, further changes may be tried with successive measurements taken for each further change to measure effectiveness in resource utilization. The length of stay statistic may comprise a percent of patient treatment experiences that are above a selected threshold over an average length of stay for a respective time-period.

Figure 4:
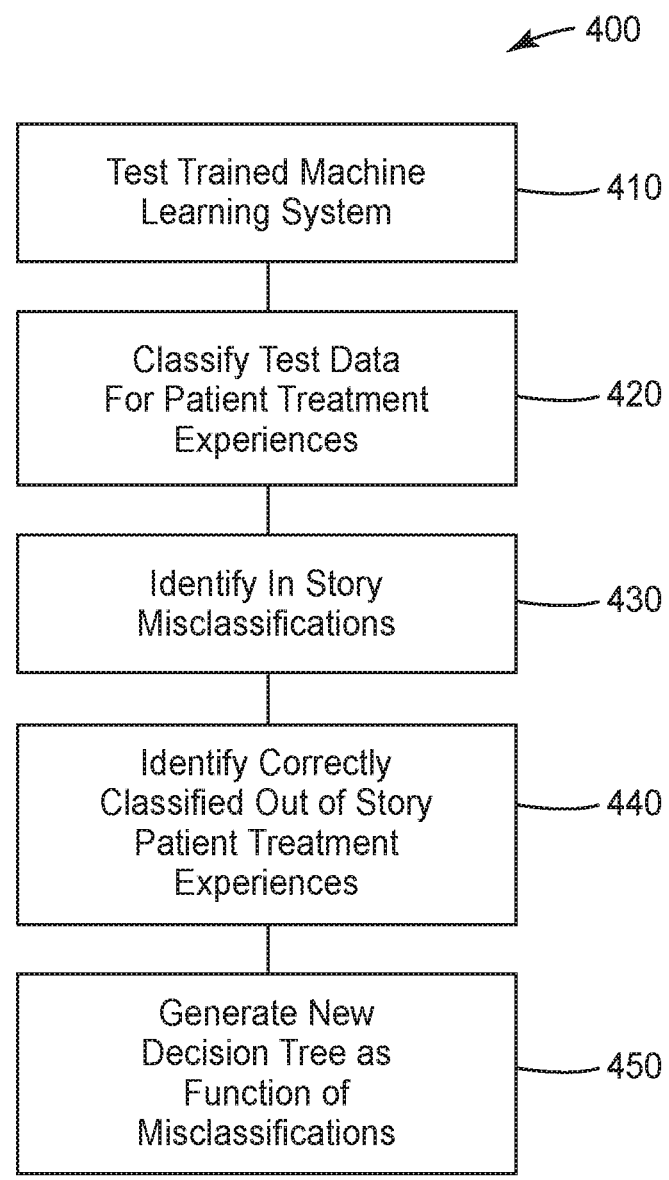
FIG. 4 is a flowchart illustrating a method of generating a further improved decision tree according to an example embodiment.

FIG. 4 is a flowchart illustrating a method 400 of generating a further improved decision tree. At operation 410, the trained machine learning system may be tested on a set of test data from the obtained data from historical patient treatment experiences. Test data patient treatment experiences may be classified via the decision tree at operation 420. At operation 430, the number of patient treatment experiences misclassified by the decision tree are identified as "in story". Operation 440 identifies the number of patient treatment experiences correctly classified by the decision tree as "out of story". Operation 450 generates a new decision tree by using cost qualifiers based on incorrectly classified in story patient treatment decisions to increase accuracy of the decision tree.

In some embodiments, machine learning systems provide the ability to execute produced decision trees against new rows of data. In one example, See5 packages come with a rule execution module that can be integrated into other software which can run the generated rules against new data rows.

If the data for a particular patient is not complete, the rules may still be executed in some embodiments. Perhaps a full coded record is not available until a formal coding is performed after the patient has been discharged. Even if this is the case, a preliminary diagnosis will be provided for the patient (which could change over time). That diagnosis and any subsequent diagnoses may be grouped to produce a preliminary DRG (diagnosis related group) while the patient is in the hospital. That data (along with any subsequent data) can be fed into the trained expert system to determine if the patient has a potential risk of going out of the norm for cost LOS (length of stay). Rules are then generated with the level of data that is available when the rules are run.

For instance, if doctors' notes at a facility are all auto-coded as soon as they are entered (prior to a final coding session by a coder), then a tentative DRG could be determined. MedSerg, serviceLine, SOI, LOS (up to that current point), admittedICU, ICUdays (to the current point), ageGroup, and weekendAdmit could also be determined from the date of admittance to the evaluation time. This data could be executed (and perhaps re-executed again and again) against the rules for a site to see if that data indicates a potential out-of-norm cost in the future.

A data store, such as database 125, associated with the rules could begin to monitor utilization even if the data is run through the rules post-discharge but before the system 100 has a chance to process the data. This could be done with a coding system, such as 3M™ 360 Encompass™ system, so as soon as codes are assigned and DRG groups are assigned, the rules could be run to determine out-of-norm costs, and a data store per facility could collect the types and categories of overruns.

In some examples, patient discharge records may be analyzed against stories where the facility or enterprise is doing well. While stories are classified as in or out of norm in the above examples and embodiments, stories may also be gathered for a whole spectrum of "doing well to doing poorly." Rules may be generated to show not only where the facility is doing poorly but also where it is excelling. Armed with that information, a facility may be better able to plan utilization of resources.

In one example, the system 100 runs a hospital's data through its measures and other code or humans may make story recommendations based on the results. The results capture the performance for a first period of time prior to implementation of changes based on the recommendations. After waiting a second period of time sufficient for the changes to take effect and collect a sufficient number of patient treatments for training and testing, data corresponding to the second time-period may be run to again and produce another set of stories—stories telling the hospital where their resource utilization out-of-norm problems are. Maybe the problems will be the same ones because they haven't fixed the ones they were previously told about, or maybe they will be a whole new slew of story problems.

In one embodiment, system 100 rules may be continuously running, even long after a patient has been discharged, to give that facility a cumulative view of the effect of working on the system-exposed problems. These rules could be running, as a matter of course, against discharged patient records to accumulate information and provide an up-to-date dashboard of how the facility is doing relative to the latest set of rules. Since discrete data is being collected, drilling down into those discrete data provides evidence of facility performance change.

When a new set of data is run through the system, a new set of rules is generated that reflects an up-to-date view of where the facility's problems are and how they are executing against them over time.

In one example analysis, a decision tree is generated for a first example set of provider data. The decision tree has a cost ratio designated that says that an "out" (in of norm)-designated story that should be "in" the story is 5 times worse than an "in"-designated story that should be "out"- designated. This, of course all depends on how the rules are being used. The error rate for this decision tree is 1%, meaning that 1% of the cases are misclassified.

Evaluation statistics:

```
       Evaluation on training data (9817 cases):
       Decision Tree
-----------------------
Size    Errors   Cost
 423   103( 1.0%)  0.01   <<
  (a)   (b)   <--classified as
----  ----
2492         (a): class in
 103  7222   (b): class out
       Options:
       Pruning confidence level 99%
       Class specified by attribute 'inStory'
       Read 9817 cases (84 attributes) from
       LOS_Test1_Story_060818.data
       Read misclassification costs from LOS_Test1_Story_060818.costs
```

The following is an example first small portion of the corresponding Decision tree:

```
eligible = f: out (518)
eligible = t:
:...admittedICU = f:
    :...PPCGroup5 = t: in (42)
    :   PPCGroup5 = f:
    :   :...PPC24 = t:
    :       :...medSurg = med: in (21)
    :       :   medSurg = surg: out (18)
    :       PPC24 = f:
    :       :...PPC48 = t: in (4/1)
    :           PPC48 = f:
    :           :...PPCGroup6 = t:
    :               :...medSurg = med: in (10)
    :               :   medSurg = surg: out (6)
    :               PPCGroup6 = f:
    :               :...PPCGroup1 =t: in (1)
    :                   PPCGroup 1 = f:
    :                   :...APRDRG in 691,5,120,56,163,20,6,196,190,4,130,162,
    :                       :    57,401,165,176,910,753,2,166,170,1,40,
    :                       :    90,774,110,770,511,911,382,841,650,51,
    :                       :    138: out (0)
...
```

The actual tree is much longer in length. The portion provided is representative of the longer tree produced by the machine learning system based on the data provided. Since data from different entities and different entity time-periods will vary, resulting decision trees will also vary.

```
       Evaluation on training data (9817 cases):
       Decision Tree
-----------------------
Size    Errors   Cost
 423   103( 1.0%)  0.01   <<
  (a)   (b)   <--classified as
----  ----
2492         (a): class in
 103  7222   (b): class out
              Attribute usage:
       100% eligible
        95% admittedICU
        94% PPCGroup6
        91% APRDRG
        55% PPC47
        54% PPC27
        39% PPCGroup5
        38% PPC24
        38% PPCGroup1
```

```
    38% PPC48
    24% soiLevel
    19% AnyPPC
    10% expLOS
     4% PPCGroup3
     4% ageGroup
     4% SOI
     3% PACfacility
     3% PPCGroup2
     2% weekendAdmit
     2% PPCGroup8
```

In a second example, boosting of the data of the first example is illustrated. Boosting works by the system generating different instances of the decision tree following slightly different generation philosophies. The final decision tree is then the combination voting of each different tree, where each have been individually run. The approach sometimes produces significant results. As in this case, the error rate on the training data is only 0.1%.

The following shows the results of "boosting" the data. Boosting causes the system to generate different decision trees for the same data. The different error rates for each of the generated decision trees may be observed, some being very good and others quite poor. The final "boosted" decision tree is subsequently not a tree per-se but the voting (and running by) of each tree against a data set. This process, as you can see below, often produced excellent results.

```
            Options:
10 boosting trials
Pruning confidence level 99%
    Class specified by attribute 'inStory'
    Read 9817 cases (84 attributes) from LOS_Test1_Story_060818.data
    Evaluation on training data (9817 cases):
    Trial    Decision Tree
    -----   ----------------
            Size     Errors
       0     328   125( 1.3%)
       1     510   499( 5.1%)
       2     525   466( 4.7%)
       3     750   913( 9.3%)
       4     697   375( 3.8%)
       5     648   353( 3.6%)
       6     536  1652(16.8%)
       7     587   893( 9.1%)
       8     699   756( 7.7%)
       9     547   558( 5.7%)
    boost          7( 0.1%)   <<
    (a)   (b)    <-classified as
    ----  ----
    2490    2    (a): class in
       5  7320   (b): class out
```

A third example contains yet another modification to the process for the first example data. In this example, the "cost" of an "out" (out of the story) record that should have been designated as an "in" (in the story) record (type II error relative to "in") to be 100 times costlier than an "in" record that should have been designated as an "out" record. This says that if a record is in the story (story meaning that these records are out of the financial norm), it's bad to say that it is out of the story. The opposite may not be as bad depending on what is being measured. Whether certain kinds of error are found as "bad" or not depends entirely on how this technology may be used in the future. For different customers, a 90 to 95% correct prediction that a patient has or may go out of the norm may or may not be acceptable. The actual error rate obtained by the system may depend on the amount of data and quality of the data used to train the system. Such error rates may be less than or greater than the rates referenced herein.

```
            Options:
    Pruning confidence level 99%
    Test requires 2 branches with >= 1 cases
        Class specified by attribute 'inStory'
        Read 148442 cases (84 attributes) from file
        Read misclassification costs from costs file
        Evaluation on training data (148442 cases):
        Decision Tree
        ----------------------
        Size    Errors   Cost
        2757  4179( 2.8%)  0.03   <<
        (a)   (b)    <-classified as
        ----- -----
        2381           (a): class in
        4179 141882    (b): class out
```

A fourth example contains a decision tree that was generated for the first set of a second provider data. The error rate for that data is 6.7%. This decision tree was tested with data from the second set of second provider data and it produced 4.3% errors, the majority of these being "in" records that were misclassified as "out" which is thought to be a more-severe form of error. The test was also reversed with the decision tree built with the second set of data and tested it with the first.

A fifth example shows those results with essentially a 0% error rate for the second provider 2 training data. The second provider 1 data run against this tree did produce a 12.1% error rate, but the majority of these were type I errors.

In this evaluation the below decision tree was built from the first set of second provider data that was received. The error rate was 6.7%, but these were all type I errors. The error rate for the test set of the second set of second provider is less at 4.3%, but most of these are type I errors. There were 21,601 training cases. Then, as part of the run, 5,186 discharge cases were processed from the second set of second provider data.

Evaluation statistics:

```
            Evaluation on training data (21601 cases):
        Decision Tree
        ----------------------
    Size     Errors    Cost
    116   1451(6.7%)   0.07   <<
    (a)   (b)    <-classified as
    ----  ----
     622          (a): class in
    1451 19528    (b): class out
            Evaluation on test data (5186 cases):
        Decision Tree
        ----------------------
    Size    Errors    Cost
    116   221( 4.3%)   1.95   <<
```

```
     (a)   (b)    <-classified as
    ----  ----
     570   202    (a): class in
      19  4395    (b): class out
Options:
    Pruning confidence level 99%
        Class specified by attribute 'inStory'
        Read 21601 cases (84 attributes) from LOS_second provider data
        Read misclassification costs from LOS second provider data costs
                    Decision tree excerpt:
    PPCGroup1 = t: out (2081)
    PPCGroup1 = f:
    :...eligible = f: out (1690)
        eligible = t:
        :...expLOS <= 2.8:
            :...cost <= 1701.89:
            :...expLOS <= 1.5:
            :   :   :...serviceLine in 165,296,90,262,294,250,293,95,45,125,274,
            :   :   :       57,283,276,145,70,135,267,387,330,390,137,
            :   :   :       272,269,133,65,252,85,170,58,
            :   :   :       1: in (0)
            :   :   serviceLine in 245,50,132,255,280: out (73)
            :   :   serviceLine = 129:
            :   :   :...weekendAdmit = f: in (12/8)
            :   :       weekendAdmit = t: out (4)
            :   expLOS > 1.5:
                ...
```

In a fifth example, the opposite of of the fourth example was done. A decision tree is built with the second provider 2 data, and is tested with the second provider 1 data set. The results are a very simple decision tree that produces only 2 type I errors and no type II errors over the 5,186 training cases. Testing the first set of Second provider data (21,601 cases) does produce a 12.1% error rate, but most of these are type I errors.

```
                        Options:
                    Pruning confidence level 99%
        Class specified by attribute 'inStory'
        Read 5186 cases (84 attributes) from LOS_Second
        providerMemorialHospital330235_Story_061918.data
        Read misclassification costs from LOS_Second
        providerMemorialHospital330235_Story_061918.costs
        Decision tree:
        eligible = f: out (468)
        eligible = t:
        :...APRDRG in 770,955,44,662,131: out (0)
            APRDRG in 640,773,425,560,135,253,244,313,403,197,461,460,383,756,141,540,
                :    222,52,720,140,194,54,139,247,45,221,241,47,566,284,663,351,710,
                :    952,58,380,861,757,309,248,263,198,776,446,463,422,225,240,204,
                :    342,137,249,134,227,136,465,199,251,224,341,346,424,468,541,382,
                :    282,626,816,308,951,850,245,723,143,317,203,220,466,207,283,51,
                :    892,41,53,254,347,115,581,246,691,279,113,82,890,364,243,281,
                :    111,228,531,501,196,660,42,421,513,694,144,344,340,724,252,130,
                :    223,614,811,264,49,262,320,190,519,950,142,760,752,813,43,462,
                :    774,361,314,205,349,138,229,542,23,500,315,482,532,384,200,362,
                :    171,740,363,423,280,261,193,791,546,711,721,661,48,242,862,722,
                :    633,305,381,514,40,55,518,755,385,50,758,26: out (3895)
            APRDRG in 750,420,201,302,754,301: in (446/2)
            APRDRG= 133:
            :...soiLevel = low: out (11)
                    Evaluation on training data (5186 cases):
                        Decision Tree
                    ----------------------
                    Size     Errors   Cost
                     13    2( 0.0%)   0.00   <<
                    (a)    (b)    <-classified as
                    ----  ----
                     772          (a): class in
                       2   4412   (b): class out
                                    Attribute usage:
                    100% eligible
                     91% APRDRG
                      7% soiLevel
                        Evaluation on test data (21601 cases):
                            Decision Tree
                        ----------------------
                        Size     Errors   Cost
                         13  2616(12.1%)   0.12   <<
```

```
    (a)    (b)   <-classified as
    ----  ----
    601    21   (a): class in
   2595 18384   (b): class out
```

A sixth example shows a decision tree for a third example facility data. The decision tree is odd because everything is declared as "out." This is because there were just 330 discharges out of 93,389 which were deemed to be "out of the norm" ('in' the story) for LOS. It appears that the third facility is doing a good job managing LOS. The system can be manipulated to create a decision three that will eliminate the 'in's that show up in the 'out's state by adding the costs factor. The error rate for this is 0.9%, however, the generated decision tree is much more complex. Out of the 93,389 discharge cases only 330 were "in" a story, or in other words out of the norm financially. Thus, there was less than 0.4% error rate for LOS management in these cases. This shows good length-of-stay management for the third facility.

```
                       Options:
              Focus on errors (ignore costs file)
           Class specified by attribute 'inStory'
           Read 93389 cases (84 attributes) from LOS_Third
           Facility_Story_061818.data
```

```
Decision tree:
    out (93389/330)
Evaluation on training data (93389 cases):
              Decision Tree
              ----------------
           Size      Errors
              1    330( 0.4%)  <<
            (a)    (b)   <-classified as
           ----  ----
            330         (a): class in
                93059   (b): class out
```

In a seventh example, an evaluation of the third facility data uses a "costs" file to designate that "ins" that were produced as "outs" were 100 times worse than not designating them that way (thus the cost). Using the "costs" qualifiers tens to create a more complex decision tree. The cost of eliminating these type II errors is a 0.9% error rate, but these come from "outs" that were misclassified as "ins".

Evaluation statistics:

```
Evaluation on training data (93389 cases):
              Decision Tree
              ----------------------
          Size    Errors   Cost
          366   862( 0.9%)  0.01  <<
          (a)    (b)   <-classified as
          ----  ----
           330          (a): class in
           862 92197    (b): class out
                       Options:
           Pruning confidence level 99%
Class specified by attribute 'inStory'
Read 93389 cases (84 attributes) from third facility data
Read misclassification costs from third facility costs data
Decision tree excerpt:
PPC40 = t:
:...medSurg = med: out (32)
:   medSurg = surg:
:   :...eligible = f: out (24)
:       eligible = t:
:       :...PPC08 =t: out (8)
:           PPC08 = f:
:           :...PPC01 = t: out (6)
:               PPC01=f:
:               :...PPC50 = t: out (6)
:                   PPC50 = f:
:                   :...APRDRG in 44,720,201,248,247,139,711,425,384,137,190,
:                   :      111,812,660,691,194,460,383,135,45,347,249,
:                   :      134,52,133,140,254,93,22,143,207,663,466,
:                   :      206,110,141,197,58,241,463,420,279,191,136,
:                   :      113,252,721,501,243,42,204,753,43,791,566,
:                   :      540,144,53,253,750,403,861,130,461,55,693,
:                   :      199,246,284,49,240,196,245,56,244,468,200,
:                   :      314,41,813,282,47,203,142,661,176,260,351,
:                   :      192,283,756,465,380,346,343,951,754,198,424,
:                   :      21,5,115,842,385,757,930,751,23,138,722,514,
:                   :      444,264,446,775,48,445,344,242,681,422,222,
              Evaluation on training data (93389 cases):
                       Decision Tree
                       ----------------------
           Size    Errors   Cost
           366   862( 0.9%)  0.01  <<
           (a)    (b)   <-classified as
           ----  ----
```

```
    330        (a): class in
862 92197     (b): class out
Attribute usage:
    100% PPC40
    100% medSurg
    100% PPC65
    72% PPC10
    71% PPC16
    71% PPC53
    71% PPC20
    71% PPC52
    71% PPC23
    71% PPC48
    71% PPC19
    71% PPC29
    71% PPC17
    71% service Line
    38% AnyPPC
    26% APRDRG
    10% expLOS
    4% cost
    3% actLOS
    2% PACfacility
    2% ageGroup
    2% admittedICU
    2% eligible
    1% weekendAdmit
    1% soiLevel
```

An eight example, contains a decision tree for data from one of a fourth entities clinics. This generation came from 770,768 discharge cases. Since the goals of See5 are to reduce the error rate (0.5% for this case) as well as reduce the complexity of the decision tree, this data achieves that goal. There are many more Type II errors (again 'in's in the 'out's category) in this tree than Type I errors ('out's in the 'in's category). If the cost of Type II errors is greater, cost parameters can be added to create a tree with these reduced.

Data from one of the fourth entity's facilities. The default decision tree that is generated is very simple. It produced a (less than) 0.5% error rate, again mostly composed of discharges that were "in" which were designated as "out" (type II errors). Again, given the low number of discharges contributing to "in" stories (3823) versus the total number of discharges (766945), this fourth entity facility seems to be doing well with its LOS management.

```
                Options:
    Focus on errors (ignore costs file)
Class specified by attribute 'inStory'
Read 770768 cases (84 attributes) from
LOS_FourthEntity_Story_061818.data
Decision tree excerpt:
PPC37 = t: out (1072/63)
PPC37 = f:
:...ICUdays <= 20: out (765920/3624)
    ICUdays > 20:
    :...facility in 3,4,5,6,7,8: out (2832/5)
        facility = 1:
        :...expLOS <= 33.8: out (392/4)
        :   expLOS > 33.8:
        :   :...expLOS <= 36.1: in (14/3)
        :       expLOS > 36.1: out (66)
        facility = 2:
        :...expLOS <= 36.1: out (406/69)
            expLOS > 36.1:
            :...weekendAdmit = t: in (16)
                weekendAdmit = f:
                :...actLOS <= 45: out (28/10)
                    actLOS > 45: in (22/1)
                        Evaluation on training data (770768 cases):
                Decision Tree
```

```
                    -continued

Size    Errors
  10    3787( 0.5%)  <<
  (a)    (b)    <-classified as
-----  -----
    40   3783   (a): class in
    4  766941   (b): class out
Attribute usage:
    100% PPC37
    100% ICUdays
    35% facility
    9% expLOS
```

A ninth example shows just the resulting statistics of adding the cost parameters to reduce the Type II errors. The generated decision tree is long and complex, so it is not shown, but as you can see the error rate is still a low 1%. With this clinic analysis, the type II errors for "in" have been reduced, but not eliminated, and there is a 1% overall error rate. Again, the type II error rate has been reduced by specifying that "ins" that have been specified as "outs" is 100 times the cost of not producing that error. The actual decision tree is quite complex and adds nothing by showing it here.

```
        Evaluation on training data (770768 cases):
            Decision Tree Size    Errors     Cost
3291   7869( 1.0%)  0.01   <<
  (a)    (b)    <-classified as
-----  -----
  3816      7   (a): class in
  7862 759083   (b): class out
```

In a tenth example, the first example data is revisited. The amount of data that went into producing them was greatly reduced. Information was eliminated to include only information that would be available from a patient stay in the training data, built the new rules, and tested them. This produced a 5.4% error rate (mostly type I errors) as opposed to the 1% that the original Tampa data produced. This does seem reasonable given the amount of data that was not available for rule generation.

This evaluation shows the results of running the system with the greatly reduced dataset. The following are the only fields that this decision tree has been trained on:
inStory.
recordID: label.
inStory: in, out.
APRDRG: discrete 317.
medSurg: med, surg.
serviceLine: discrete 41.
soiLevel: low, high.
SOI: U,L,M,H,X.
eligible: f,t.
actLOS: continuous.
expLOS: continuous.
admittedICU: f,t.
ICUdays: continuous.
ageGroup: under65, 65to74, 75to84, over84.
weekendAdmit: f,t.

The intent of this data is to reduce the fields to only those that may be available during a patient stay. Again, this absolutely presumes that concurrent auto-coding and DRG generation are performed while the patient is in the hospital or in a timely manner based on the use of the data.

```
Here are the evaluation statistics:
Evaluation on training data (9817 cases):
        Decision Tree
        -----------------------
Size    Errors    Cost
 730   530( 5.4%)  0.07  <<
 (a)    (b)    <-classified as
 ----  ----
 2464   28    (a): class in
  502  6823   (b): class out
Attribute usage:
    100% eligible
     95% APRDRG
     95% admittedICU
     49% expLOS
     31% soiLevel
     18% actLOS
     18% ageGroup
     12% ICUdays
     10% weekendAdmit
      8% SOI
```

Though the decision tree is quite long, the use of the DRG early in the evaluation is of note. As can also be seen above the DRG is used in 95% of the decision tree logic.

```
Options:
    Pruning confidence level 99%
    Test requires 2 branches with >= 1 cases
Class specified by attribute 'inStory'
Read 9817 cases (84 attributes) from LOS_Test1_Story_060818.data
Read misclassification costs from LOS_Test1_Story_060818.costs
Decision tree excerpt:
eligible = f: out (518)
eligible = t:
:...admittedICU = f:
   :...expLOS <= 2.2:
      : :...APRDRG in 50,194,691,463,5,139,440,260,120,301,55,56,141,720,420,
      : :         791,312,45,756,383,173,302,346,952,180,140,711,384,263,
      : :         42,460,44,174,136,254,163,199,815,137,191,244,281,261,
      : :         143,951,662,710,52,197,466,264,169,221,58,133,248,468,
      : :         20,950,842,241,253,46,724,844,681,80,308,171,309,246,
      : :         364,6,226,196,227,813,252,282,48,443,344,303,21,284,660,
      : :         224,247,92,755,447,23,380,190,243,347,757,279,283,349,
      : :         167,220,4,313,721,385,775,351,223,444,424,530,229,130,
      : :         134,161,850,121,240,930,162,912,442,305,57,314,43,401,
      : :         441,540,462,304,425,423,165,693,176,722,381,694,361,245,
      : :         910,860,753,262,340,723,501,2,862,166,170,680,461,142,
      : :         531,341,135,193,843,1,225,40,280,894,205,91,26,317,892,
      : :         421,651,90,774,690,22,41,110,770,343,661,518,511,751,
      : :         177,911,89,776,563,773,510,131,561,382,890,49,405,893,
      : :         841,517,750,500,650,692,51,138: in (0)
      : :   APRDRG in 315,316,201,82,73,115,251,198,175,812,204,113,24,422,
      : :         203,310,320,206,54,114,111,519,144,47,207,192,861,249,
      : :         465,404,98,222,566,560,70,512,532,242,513,811,362,200,
      : :         363,97,93,228,484: out (131)
      : :   APRDRG in 53,816,446,342,403,481,482,445,480: in (53)
      : :   APRDRG = 663:
      : :   :...ageGroup = under65: in (1)
      : :      ageGroup in 65to74,75to84,over84: out (3)
            Evaluation on training data (9817 cases):
               Decision Tree
            -----------------------
Size    Errors    Cost
 730   530( 5.4%)  0.07  <<
 (a)    (b)    <-classified as
 ----  ----
 2464   28    (a): class in
  502  6823   (b): class out
Attribute usage:
    100% eligible
     95% APRDRG
     95% admittedICU
     49% expLOS
     31% soiLevel
```

```
18% actLOS
18% ageGroup
12% ICUdays
10% weekendAdmit
 8% SOI
```

In an eleventh example, the second provider data is revisited by building the rules from the second provider 1 data set again, but building them using the same reduced schema used above. That data and the second provider 2 data was run through the rules comprising the model/decision tree. Surprisingly the training data (second provider 1) produced an 8.4% error rate (mostly type I errors) while the second provider 2 test data (reduced as well) produced only a 4.1% error rate.

In this test, rules were generated utilizing the reduced set of Second provider 1 data. Statistics are shown for that generation and also Second provider 2 data run against these reduced set of rules.

```
Test statistics:
Evaluation on training data (21601 cases):
        Decision Tree
    -----------------
    Size      Errors     Cost
     61    1822( 8.4%)   0.08   <<
     (a)    (b)   <-classified as
    ----   ----
    622         (a): class in
    1822 19157  (b): class out
Attribute usage:
    100% eligible
     91% expLOS
     63% APRDRG
     29% serviceLine
      9% soiLevel
      7% ageGroup
      5% admittedICU
      2% actLOS
      2% weekendAdmit
        Evaluation on test data (5186 cases):
            Decision Tree
        -----------------
        Size      Errors     Cost
         61    213( 4.1%)   3.74   <<
         (a)    (b)   <-classified as
        ----   ----
         578   194    (a): class in
          19  4395    (b): class out
```

This is interesting that the secondary data produced a smaller percentage of errors though they were mostly of type II errors. Here is the decision tree and all statistics for the run:

```
Options:
    Pruning confidence level 99%
Class specified by attribute 'inStory'
Read 21601 cases (84 attributes) from LOS_Second provider data
Read misclassification costs from LOS_Second provider costs data
Decision tree excerpt:
eligible = f: out (1880)
eligible = t:
:...expLOS <= 2.8:
    :...serviceLine in 294,293,267,269,133,252,85,170,58,1: out (0)
    :   serviceLine in 245,165,296,90,50,262,250,95,45,125,132,274,255,57,283,
    :   :             276,280,145,70,135,387,330,390,137,272,
    :   :             65: out(6214)
    :   serviceLine = 129:
    :   :...APRDRG in 640,383,139,425,720,140,201,133,560,774,468,750,420,773,
    :                 190,204,540,247,135,253,244,313,42,952,171,710,463,282,
    :                 113,194,137,142,308,143,753,130,302,341,460,754,224,115,
    :                 249,566,751,198,46,347,45,111,951,207,254,403,54,141,
    :                 663,55,380,513,144,252,44,281,284,136,775,757,446,776,
    :                 351,722,589,245,263,301,251,342,755,248,53,421,279,581,
    :                 241,723,221,206,197,47,484,660,196,423,317,243,465,283,
    :                 225,950,690,246,531,52,385,721,315,422,82,48,134,203,
    :                 340,57,691,349,384,58,138,304,240,424,500,223,227,843,
    :                 791,226,694,242,364,228,343,51,346,661,626,309,80,756,
    :                 305,49,344,199,614,561,758,110,541,50,466,752,310,760,
    :                 518,381,176,262,724,314,321,633,200,483,532,461,514,501,
    :                 41,442,563,681,43,441,930,280,512,316,565,445,361,220,
    :                 564,180,912,510,222,519,404,170,121,205,320,229,544,382,
    :                 711,131,114,443,636,405,362,26,650,98,892,546,639,56,
    :                 193,770,482,191,530,862,850,890,264,462,955,542,23,740,
    :                 363,261,662,40,680,167,894,447,517,260,
    :                 844: in (0)
    :   APRDRG in 861,816,815,813,811: out (42)
    :   APRDRG = 812:
            ...
            Evaluation on training data (21601 cases):
                Decision Tree
            -----------------
            Size      Errors     Cost
             61    1822( 8.4%)   0.08   <<
```

```
            (a)    (b)    <-classified as
           ----   ----
            622          (a): class in
           1822  19157   (b): class out
      Attribute usage:
           100% eligible
            91% expLOS
            63% APRDRG
            29% serviceLine
             9% soiLevel
             7% ageGroup
             5% admittedICU
             2% actLOS
             2% weekendAdmit
                 Evaluation on test data (5186 cases):
              Decision Tree
      ----------------------
      Size    Errors    Cost
       61    213( 4.1%)  3.74  <<
       (a)    (b)   <-classified as
      ----    ----
       578    194   (a): class in
        19   4395   (b): class out
```

In a twelfth example, the results of running the latest second provider data (Second provider 3) through the system are shown. The error rate is a very small 0.1%. Of particular note is that of the 5,164 Patient discharges that were included in this data set 34% (1309) of the patients contributed to the "in" story. Or in other words, 34% of these had LOSs which were out of the norm. This hospital surely needs help.

In this evaluation, the latest second provider data is processed to produce a simple decision tree that models that latest data with a 0.1% error rate. As with the other second provider data, all produced simple decision trees. This set of data possessed 34% of the records that fed into the story (out of norm) which is high. There is definite room for LOS improvement with this site.

```
                          Options:
                Pruning confidence level 99%
   Class specified by attribute 'inStory'
   Read 5164 cases (84 attributes) from LOS_SECOND PROVIDER data
   Decision tree excerpt:
   expLOS <= 2:
   :...expLOS <= 1.7: out (32/2)
   :   expLOS > 1.7:
   :   :...serviceLine in 296,165,294,250,245,293,90,267,274,57,330,276,145,95,
   :   :         137,252,70,272,85,65,170,133,58: in (0)
   :       serviceLine in 262,132: in (316/1)
   :       serviceLine in 129,125,387,255,283,135,45,280,390: out (34)
   :       serviceLine = 50:
   :       :...admittedICU = f: out (12)
   :           admittedICU = t: in (43)
   expLOS > 2:
   :...admittedICU = f:
       :...expLOS <= 7:
          :  :...PPCGroup8 =t:
          :  :  :...medSurg = med: out (4)
          :  :  :   medSurg = surg: in (12)
          :  :  PPCGroup8 = f:
          :  :  :...APRDRG in 750,710,500,757,203,130,49,252,362,317,57,951,650,
          :  :  :           912,723,950,364,305,82,46,98,465,791,343,565,205,
          :  :  :           892,441,681,811,815,952,50,309,581,280,224,115,544,
          :  :  :           310,691,930,382,121,442,519,443,191,445,
          :  :  :       :  :  862: out (0)
                 Evaluation on training data (5164 cases):
              Decision Tree
              ---------------
          Size     Errors
           44    7( 0.1%)  <<
           (a)    (b)   <-classified as
          ----   ----
          1305     3    (a): class in
             4  3852    (b): class out
      Attribute usage:
           100% expLOS
            93% admittedICU
            64% APRDRG
            55% PPCGroup8
            40% serviceLine
```

-continued

```
    12% soiLevel
     4% eligible
```

A thirteenth example shows the same latest second provider data (second provider 3) but processed by a 10-fold cross-validation of the data. What this means is that 10 random subsets of the data are taken where, in this case, 75% of the data is used for training a decision tree and 25% of the subset is used to test the trained decision tree. As was said, 10 of these are created and tested and the resulting statistics are averaged together to give an estimated average error rate. The mean error rate turned out to be 2.3% with a standard error of 0.3%. These numbers are quite a bit higher than the "untested" 0.1% error rate from example 12, but they are statistically more in line with likely numbers produced for further untested data for Second provider.

```
              Options:
         Use 75% of data for training
         Pruning confidence level 99%
         Cross-validate using 10 folds
Class specified by attribute 'inStory'
Read 3873 cases (84 attributes) from LOS_SECOND PROVIDER data
Read misclassification costs from LOS_SECOND PROVIDER costs data
[ Fold 1 ]
Decision tree excerpt:
eligible = f: out (282)
eligible = t:
:...APRDRG in 49,55,321,317,912,950,98,563,196,565,205,811,813,110,510,193,
  :        770,191,530: in (0)
   APRDRG in 774,301,753,203,776,198,206,252,207,315,190,773,309,
  :        280: in (180/7)
   APRDRG in 468,812,383,640,540,751,221,710,421,500,756,302,757,463,171,140,
  :        139,446,351,134,53,466,45,425,137,135,246,861,711,304,111,724,
  :        422,349,263,229,42,130,283,54,663,362,754,420,340,240,57,58,531,
  :        513,197,721,314,26,380,141,44,136,251,951,342,47,143,650,723,
  :        364,226,305,82,46,114,566,228,225,755,347,465,142,313,223,385,
  :        791,384,113,343,424,758,661,227,816,222,541,281,483,138,41,461,
  :        341,501,722,892,441,346,681,561,43,815,144,48,690,952,344,50,
  :        660,581,381,633,626,224,546,80,639,115,544,310,691,930,56,382,
  :        121,200,220,752,442,519,262,482,760,443,51,512,445,
  :       862: out (1799)
         Evaluation on hold-out data (388 cases):
         Decision Tree
         ----------------------
       Size   Errors  Cost
        65   11( 2.8%)  0.03  <<
[ Summary ]
Fold      Decision Tree
----      ----------------------
       Size   Errors  Cost
  1     60    2.6%   0.05
  2     66    0.8%   0.01
  3     63    3.1%   0.05
  4     66    1.3%   0.01
  5     60    2.6%   0.05
  6     66    3.1%   0.03
  7     63    3.1%   0.05
  8     66    2.3%   0.02
  9     66    1.5%   0.06
 10     65    2.8%   0.03
Mean   64.1   2.3%   0.04
SE      0.8   0.3%   0.01
         (a)   (b)   <–classified as
         ----  ----
         977     6   (a): class in
          84  2806   (b): class out
```

Automatically-generating rules is a viable approach for synthesizing, encompassing, and deploying machine-learned "knowledge" that shows that a patient has or possibly will go "out of the norm" for the cost for a medical situation for various types of metrics, such as LOS. Rules, especially rules written in a textual way that conveys the logical antecedent and consequent of those rules, can be very useful if human understanding of the logic is required. This surface understanding, however, can quickly become a mirage of knowledge. Rules can give the impression that a person can somehow understand the underlying processing or process that is occurring.

Humans may understand the underlining process if the rules are small, the number of rules is not great, or the number of variables involved in each rule is not considerable. As can be seen by the above examples, usually none of these conditions is true. Humans often get a false sense that they can understand the rules when in fact the logic the rules or model convey is beyond our comprehension.

In some embodiments, deep learning neural networks may be trained to produce a model to predict LOS or other metrics. If sufficiently trained, neural networks can fire (determine "out of norm" or not) on minimal data. The above example decision trees comprised of rules will only fire the consequent of a rule if the antecedent of that rule is entirely and precisely met. Neural networks can be trained to fire with less data while showing that the strength of that firing is less. Neural networks, if trained with deep layers, can find nuance in the data—relationships of data and outcomes—that rules may never demonstrate and that humans are incapable of finding.

Neural networks and especially deep neural networks are a black box. One can look at the weights of the connections of the neurons and never know what any of it really means. With the above decision tree rules, a human can look at, think about, and consider the ramification of the rules. Neural networks just feed data to and see what comes out. You will never know why it comes up with outputs—other than the training data possessed the "shadow" of that relationship. Deep neural network processing is practical because of the speed and ubiquity of parallel processors that can simultaneously perform large numbers of matrix multiplications.

The use of deep neural networks for predicting one or more metrics will allow recognition of greater nuance in the variables which point to in/out of norm. Groupings and relationships of the variables that indicate in/out of norm may be detected with greater specificity.

Artificial intelligence (AI) is a field concerned with developing decision-making systems to perform cognitive tasks that have traditionally required a living actor, such as a person. Artificial neural networks (ANNs) are computational structures that are loosely modeled on biological neurons. Generally, ANNs encode information (e.g., data or decision making) via weighted connections (e.g., synapses) between nodes (e.g., neurons). Modern ANNs are foundational to many AI applications, such as automated perception (e.g., computer vision, speech recognition, contextual awareness, etc.), automated cognition (e.g., decision-making, logistics, routing, supply chain optimization, etc.), automated control (e.g., autonomous cars, drones, robots, etc.), among others.

Many ANNs are represented as matrices of weights that correspond to the modeled connections. ANNs operate by accepting data into a set of input neurons that often have many outgoing connections to other neurons. At each traversal between neurons, the corresponding weight modifies the input and is tested against a threshold at the destination neuron. If the weighted value exceeds the threshold, the value is again weighted, or transformed through a nonlinear function, and transmitted to another neuron further down the ANN graph—if the threshold is not exceeded then, generally, the value is not transmitted to a down-graph neuron and the synaptic connection remains inactive. The process of weighting and testing continues until an output neuron is reached; the pattern and values of the output neurons constituting the result of the ANN processing.

The correct operation of most ANNs relies on correct weights. However, ANN designers do not generally know which weights will work for a given application. Instead, a training process is used to arrive at appropriate weights. ANN designers typically choose a number of neuron layers or specific connections between layers including circular connection, but the ANN designer does not generally know which weights will work for a given application. Instead, a training process generally proceeds by selecting initial weights, which may be randomly selected. Training data is fed into the ANN and results are compared to an objective function that provides an indication of error. The error indication is a measure of how wrong the ANN's result was compared to an expected result. This error is then used to correct the weights. Over many iterations, the weights will collectively converge to encode the operational data into the ANN. This process may be called an optimization of the objective function (e.g., a cost or loss function), whereby the cost or loss is minimized.

A gradient descent technique is often used to perform the objective function optimization. A gradient (e.g., partial derivative) is computed with respect to layer parameters (e.g., aspects of the weight) to provide a direction, and possibly a degree, of correction, but does not result in a single correction to set the weight to a "correct" value. That is, via several iterations, the weight will move towards the "correct," or operationally useful, value. In some implementations, the amount, or step size, of movement is fixed (e.g., the same from iteration to iteration). Small step sizes tend to take a long time to converge, whereas large step sizes may oscillate around the correct value, or exhibit other undesirable behavior. Variable step sizes may be attempted to provide faster convergence without the downsides of large step sizes.

Backpropagation is a technique whereby training data is fed forward through the ANN—here "forward" means that the data starts at the input neurons and follows the directed graph of neuron connections until the output neurons are reached—and the objective function is applied backwards through the ANN to correct the synapse weights. At each step in the backpropagation process, the result of the previous step is used to correct a weight. Thus, the result of the output neuron correction is applied to a neuron that connects to the output neuron, and so forth until the input neurons are reached. Backpropagation has become a popular technique to train a variety of ANNs.

Figure 5:
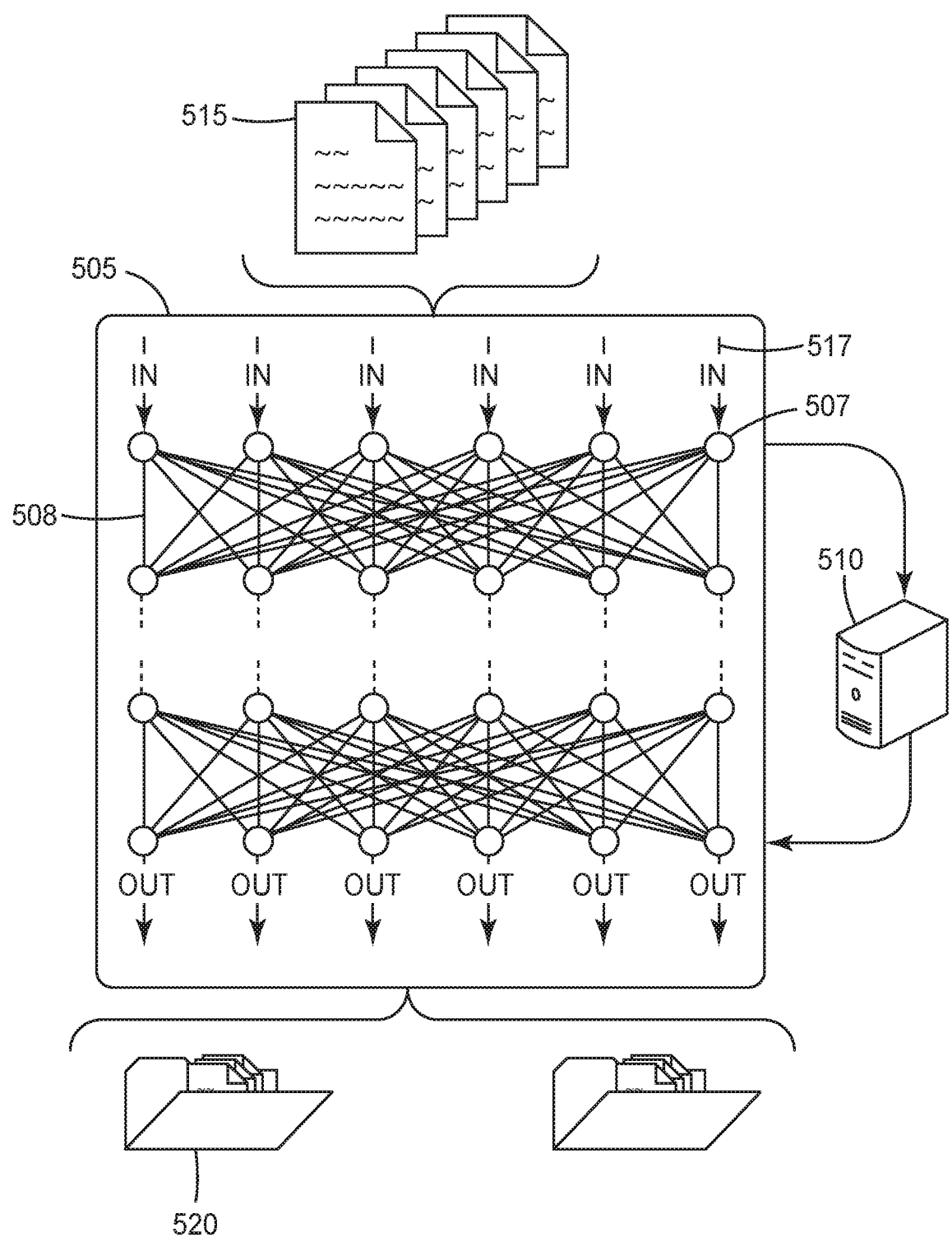
FIG. 5 is a block diagram of an example of an environment including a system for neural network training according to an example embodiment.

FIG. 5 is a block diagram of an example of an environment including a system for neural network training, according to an embodiment. The system includes an ANN 505 that is trained using a processing node 510. The processing node 510 may be a CPU, GPU, field programmable gate array (FPGA), digital signal processor (DSP), application specific integrated circuit (ASIC), or other processing circuitry. In an example, multiple processing nodes may be employed to train different layers of the ANN 505, or even different nodes 507 within layers. Thus, a set of processing nodes 510 is arranged to perform the training of the ANN 505.

The set of processing nodes 510 is arranged to receive a training set 515 for the ANN 505. The ANN 505 comprises a set of nodes 507 arranged in layers (illustrated as rows of nodes 507) and a set of inter-node weights 508 (e.g., parameters) between nodes in the set of nodes. In an example, the training set 515 is a subset of a complete training set. Here, the subset may enable processing nodes with limited storage resources to participate in training the ANN 505.

The training data may include multiple numerical values representative of a domain, such as red, green, and blue pixel values and intensity values for an image or pitch and volume values at discrete times for speech recognition. Each value of the training, or input 517 to be classified once ANN 505 is trained, is provided to a corresponding node 507 in the first layer or input layer of ANN 505. The values propagate through the layers and are changed by the objective function.

As noted above, the set of processing nodes is arranged to train the neural network to create a trained neural network. Once trained, data input into the ANN will produce valid classifications 520 (e.g., the input data 517 will be assigned into categories), for example. The training performed by the set of processing nodes 507 is iterative. In an example, each iteration of the training of the neural network is performed independently between layers of the ANN 505. Thus, two distinct layers may be processed in parallel by different members of the set of processing nodes. In an example, different layers of the ANN 505 are trained on different hardware. The members of different members of the set of processing nodes may be located in different packages, housings, computers, cloud based resources, etc. In an example, each iteration of the training is performed independently between nodes in the set of nodes. This example is an additional parallelization whereby individual nodes 507 (e.g., neurons) are trained independently. In an example, the nodes are trained on different hardware.

Figure 6:
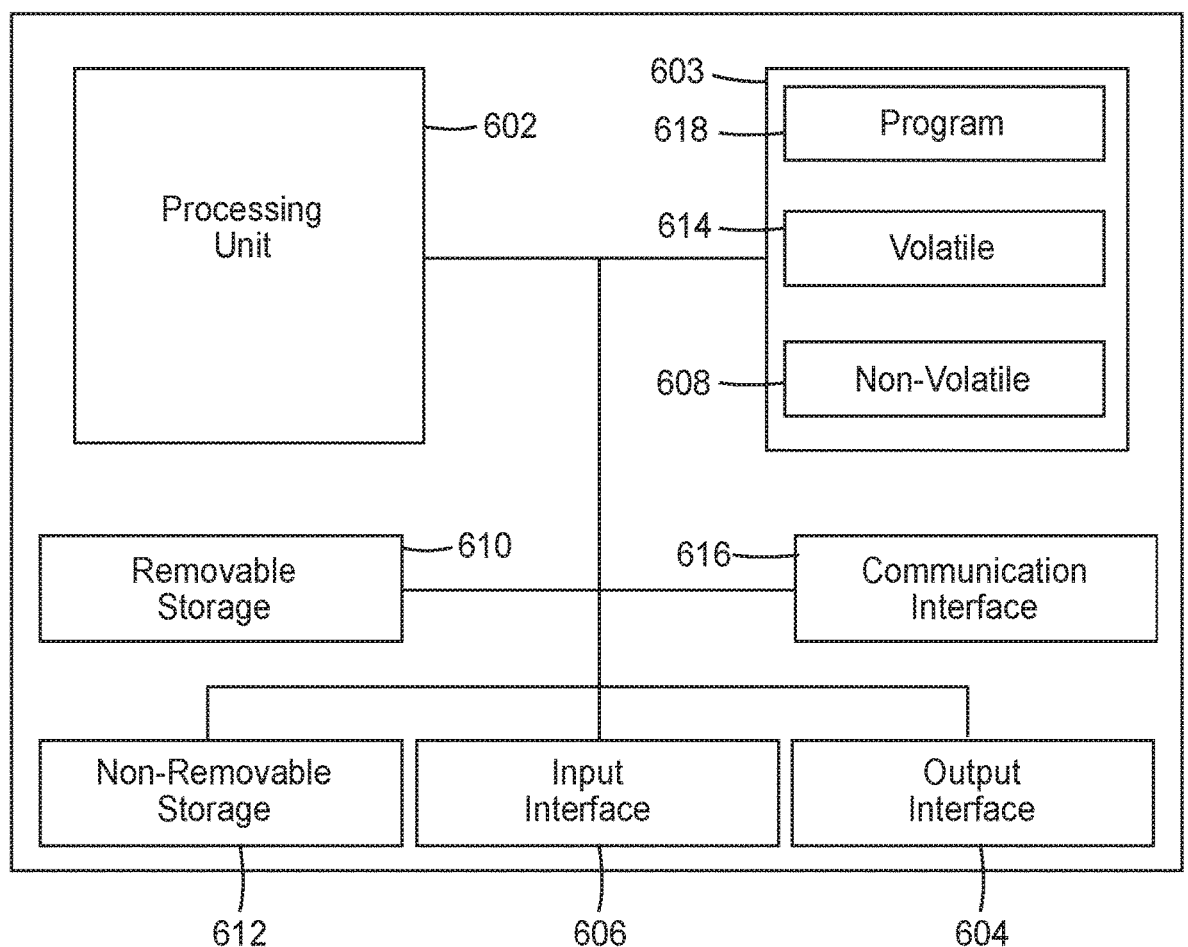
FIG. 6 is a block schematic diagram of a computer system to implement device and methods for implementing the database platform according to an example embodiment.

FIG. 6 is a block schematic diagram of a computer system 600 to implement device and methods for implementing the database platform, including the expert system, and decision trees, and performing methods and algorithms according to example embodiments. All components need not be used in various embodiments. One example computing device in the form of a computer 600 may include a processing unit 602, memory 603, removable storage 610, and non-removable storage 612. Although the example computing device is illustrated and described as computer 600, the computing device may be in different forms in different embodiments. For example, the computing device may instead be a smartphone, a tablet, smartwatch, smart storage device (SSD), or other computing device including the same or similar elements as illustrated and described with regard to FIG. 6. Devices, such as smartphones, tablets, and smartwatches, are generally collectively referred to as mobile devices or user equipment.

Although the various data storage elements are illustrated as part of the computer 600, the storage may also or alternatively include cloud-based storage accessible via a network, such as the Internet or server-based storage. Note also that an SSD may include a processor on which the parser may be run, allowing transfer of parsed, filtered data through I/O channels between the SSD and main memory.

Memory 603 may include volatile memory 614 and non-volatile memory 608. Computer 600 may include—or have access to a computing environment that includes—a variety of computer-readable media, such as volatile memory 614 and non-volatile memory 608, removable storage 610 and non-removable storage 612. Computer storage includes random access memory (RAM), read only memory (ROM), erasable programmable read-only memory (EPROM) or electrically erasable programmable read-only memory (EEPROM), flash memory or other memory technologies, compact disc read-only memory (CD ROM), Digital Versatile Disks (DVD) or other optical disk storage, magnetic cassettes, magnetic tape, magnetic disk storage or other magnetic storage devices, or any other medium capable of storing computer-readable instructions.

Computer 600 may include or have access to a computing environment that includes input interface 606, output interface 604, and a communication interface 616. Output interface 604 may include a display device, such as a touchscreen, that also may serve as an input device. The input interface 606 may include one or more of a touchscreen, touchpad, mouse, keyboard, camera, one or more device-specific buttons, one or more sensors integrated within or coupled via wired or wireless data connections to the computer 600, and other input devices. The computer may operate in a networked environment using a communication connection to connect to one or more remote computers, such as database servers. The remote computer may include a personal computer (PC), server, router, network PC, a peer device or other common data flow network switch, or the like. The communication connection may include a Local Area Network (LAN), a Wide Area Network (WAN), cellular, Wi-Fi, Bluetooth, or other networks. According to one embodiment, the various components of computer 600 are connected with a system bus 620.

Computer-readable instructions stored on a computer-readable medium are executable by the processing unit 602 of the computer 600, such as a program 618. The program 618 in some embodiments comprises software to implement one or more of the database platform, expert system, and other methods and operations described herein. A hard drive, CD-ROM, and RAM are some examples of articles including a non-transitory computer-readable medium such as a storage device. The terms computer-readable medium and storage device do not include carrier waves to the extent carrier waves are deemed too transitory. Storage can also include networked storage, such as a storage area network (SAN). Computer program 618 along with the workspace manager 622 may be used to cause processing unit 602 to perform one or more methods or algorithms described herein.

Although a few embodiments have been described in detail above, other modifications are possible. For example, the logic flows depicted in the figures do not require the particular order shown, or sequential order, to achieve desirable results. Other steps may be provided, or steps may be eliminated, from the described flows, and other components may be added to, or removed from, the described systems. Other embodiments may be within the scope of the following claims.

The following statements are potential claims that may be converted to claims in a future application. No modification of the following statements should be allowed to affect the interpretation of claims which may be drafted when this provisional application is converted into a regular utility application.

The invention claimed is:

1. A computer implemented method comprising:
   obtaining a schema defining variables representing patient treatment experiences for one or more health conditions, wherein the treatment experiences include a length of stay corresponding to a patient treatment procedure;

obtaining data from historical patient treatment experiences, the data being arranged in accordance with the schema and corresponding to a single health care facility;

training a machine learning system based on a training set of the data for a specified time-period, wherein the specified time-period comprises a time-period starting from a time following a change in procedures at the single health care facility;

generating a model from the trained machine learning system, the model being based on variables selected by the trained machine learning system to predict patient treatment experiences for the one or more health conditions;

generating a first length of stay statistic for a first time-period prior to the change in procedures;

generating a second length of stay statistic for a second time-period following the change in procedures; and determining the effectiveness of the change in procedures as a function of the length of stay statistics.

2. The method of claim 1 wherein the length of stay statistic comprises a percent of patient treatment experiences that are above a selected threshold over an average length of stay for a respective time-period.

3. The method of claim 1 and further comprising testing the trained machine learning system on a set of test data from the obtained data from historical patient treatment experiences, wherein the model comprises a decision tree including multiple rules.

4. The method of claim 3 and further comprising:
classifying test data patient treatment experiences via the decision tree;
identifying the number of patient treatment experiences misclassified by the decision tree as "in story";
identifying the number of patient treatment experiences correctly classified by the decision tree is "out of story"; and
generating a new decision tree by using cost qualifiers based on incorrectly classified in story patient treatment decisions to increase accuracy of the decision tree.

5. The method of claim 1, wherein the model comprises a decision tree including multiple rules and further comprising pruning the decision tree as a function of attribute usage in the decision tree.

6. The method of claim 1, wherein the model comprises a decision tree including multiple rules and further comprising boosting the decision tree by generating multiple different decision trees from the trained machine learning system and combining results from the multiple different decision trees to predict patient treatment experiences for the one or more health conditions.

7. The method of claim 1 wherein the data is stored in a database in accordance with a schema defining the data comprising:
a dependent variable name and corresponding discrete value selected from a set of discrete values;
a first set of multiple independent variables having corresponding discrete values; and
at least one independent variable having a corresponding continuous value.

8. A machine-readable storage device having instructions for execution by a processor of the machine to perform operations comprising:
obtaining a schema defining variables representing patient treatment experiences for one or more health conditions, wherein the treatment experiences include a length of stay corresponding to a patient treatment procedure;
obtaining data from historical patient treatment experiences, the data being arranged in accordance with the schema and corresponding to a single health care facility;
training a machine learning system based on a training set of the data for a specified time-period, wherein the specified time-period comprises a time-period starting from a time following a change in procedures at the single health care facility;
generating a model from the trained machine learning system, the model being based on variables selected by the trained machine learning system to predict patient treatment experiences for the one or more health conditions;
generating a first length of stay statistic for a first time-period prior to the change in procedures;
generating a second length of stay statistic for a second time-period following the change in procedures; and
determining the effectiveness of the change in procedures as a function of the length of stay statistics.

9. The machine-readable storage device of claim 8, wherein the length of stay statistic comprises a percent of patient treatment experiences that are above a selected threshold over an average length of stay for a respective time-period.

10. The machine-readable storage device of claim 8, wherein the model comprises a decision tree including multiple rules wherein the operations further comprise:
testing the trained machine learning system on a set of test data from the obtained data from historical patient treatment experiences;
classifying test data patient treatment experiences via the decision tree;
identifying the number of patient treatment experiences misclassified by the decision tree as "in story";
identifying the number of patient treatment experiences correctly classified by the decision tree is "out of story"; and
generating a new decision tree by using cost qualifiers based on incorrectly classified in story patient treatment decisions to increase accuracy of the decision tree.

11. A device comprising:
a processor and a memory device coupled to the processor and having a program stored thereon for execution by the processor to perform operations comprising:
obtaining a schema defining variables representing patient treatment experiences for one or more health conditions, wherein the treatment experiences include a length of stay corresponding to a patient treatment procedure;
obtaining data from historical patient treatment experiences, the data being arranged in accordance with the schema and corresponding to a single health care facility;
training a machine learning system based on a training set of the data for a specified time-period, wherein the specified time-period comprises a time-period starting from a time following a change in procedures at the single health care facility;
generating a model from the trained machine learning system, the model being based on variables selected by the trained machine learning system to predict patient treatment experiences for the one or more health conditions;

generating a first length of stay statistic for a first time-period prior to the change in procedures;

generating a second length of stay statistic for a second time-period following the change in procedures; and determining the effectiveness of the change in procedures as a function of the length of stay statistics.

12. The device of claim 11 wherein the length of stay statistic comprises a percent of patient treatment experiences that are above a selected threshold over an average length of stay for a respective time-period.

13. The device of claim 11, wherein the model comprises a decision tree including multiple rules and wherein the operations further comprise:

testing the trained machine learning system on a set of test data from the obtained data from historical patient treatment experiences;

classifying test data patient treatment experiences via the decision tree;

identifying the number of patient treatment experiences misclassified by the decision tree as "in story";

identifying the number of patient treatment experiences correctly classified by the decision tree is "out of story"; and generating a new decision tree by using cost qualifiers based on incorrectly classified in story patient treatment decisions to increase accuracy of the decision tree.

14. The machine-readable storage device of claim 8, wherein the model comprises a decision tree including multiple rules and further comprising pruning the decision tree as a function of attribute usage in the decision tree.

15. The machine-readable storage device of claim 8, wherein the model comprises a decision tree including multiple rules and further comprising boosting the decision tree by generating multiple different decision trees from the trained machine learning system and combining results from the multiple different decision trees to predict patient treatment experiences for the one or more health conditions.

16. The machine-readable storage device of claim 8, wherein the data is stored in a database in accordance with a schema defining the data comprising:

a dependent variable name and corresponding discrete value selected from a set of discrete values;

a first set of multiple independent variables having corresponding discrete values; and at least one independent variable having a corresponding continuous value.

17. The device of claim 11, wherein the model comprises a decision tree including multiple rules and further comprising pruning the decision tree as a function of attribute usage in the decision tree.

18. The device of claim 11, wherein the model comprises a decision tree including multiple rules and further comprising boosting the decision tree by generating multiple different decision trees from the trained machine learning system and combining results from the multiple different decision trees to predict patient treatment experiences for the one or more health conditions.

19. The device of claim 11, wherein the data is stored in a database in accordance with a schema defining the data comprising:

a dependent variable name and corresponding discrete value selected from a set of discrete values;

a first set of multiple independent variables having corresponding discrete values; and at least one independent variable having a corresponding continuous value.

* * * * *